United States Patent [19]

Jensen-Korte et al.

[11] Patent Number: 4,931,461
[45] Date of Patent: Jun. 5, 1990

[54] PESTICIDAL SUBSTITUTED 5-METHYLAMINO-1-ARYLPYRAZOLES

[75] Inventors: Uta Jensen-Korte, Duesseldorf; Otto Schallner, Monheim; Jörg Stetter, Wuppertal; Benedikt Becker, Mettmann; Wolfgang Behrenz, Overath; Wilhelm Stendel; Peter Andrews, both of Wuppertal, all of Fed. Rep. of Germany

[73] Assignee: Bayer Aktiengesellschaft, Leverkusen, Fed. Rep. of Germany

[21] Appl. No.: 203,358

[22] Filed: Jun. 6, 1988

[30] Foreign Application Priority Data

Jun. 12, 1987 [DE] Fed. Rep. of Germany ....... 3719732

[51] Int. Cl.⁵ .................... A01N 43/56; C07D 231/44
[52] U.S. Cl. ..................... 514/404; 514/407; 548/362; 548/376
[58] Field of Search ................ 548/376, 362; 514/404, 514/407

[56] References Cited

U.S. PATENT DOCUMENTS 4,771,066 9/1988 Gehring et al. ............... 514/407
4,804,675 2/1989 Jensen-Korte ................ 514/407

*Primary Examiner*—Robert W. Ramsuer
*Attorney, Agent, or Firm*—Sprung, Horn, Kramer & Woods

[57] ABSTRACT

Pesticidal substituted 5-methylamino-1-arylpyrazoles of the formula

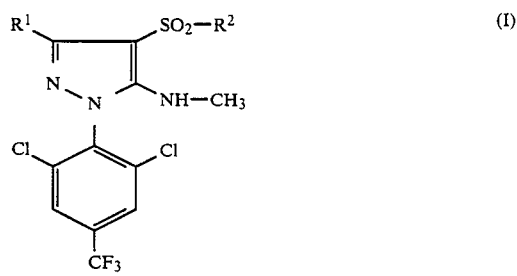

in which
  $R^1$ represents alkyl, and
  $R^2$ represents halogenoalkyl.

3 Claims, No Drawings

PESTICIDAL SUBSTITUTED 5-METHYLAMINO-1-ARYLPYRAZOLES

The invention relates to new substituted 5-methylamino-1-arylpyrazoles, several processes for their preparation and their use as pest-combating agents.

It has already been disclosed that certain 1-aryl-pyrazoles, such as, for example, 1-(2,6-dichloro-4-trifluoromethylphenyl)-5-methylamino-4-trifluoromethylthio-pyrazole or 1-(2,6-dichloro-4-trifluoromethylphenyl)-5-methylamino-4-dichlorofluoromethylthio-pyrazole possess insecticidal, acaricidal and nematicidal properties (compare EP 201,852).

However, the activity of these previously known compounds is not completely satisfactory in all areas of application, in particular at low application rates and concentrations.

New 1-arylpyrazoles of the general formula (I)

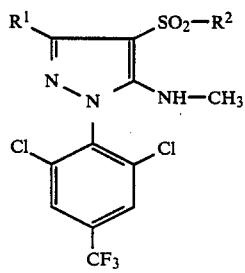

in which
$R^1$ represents alkyl and
$R^2$ represents halogenoalkyl,
have been found.

Furthermore, it has been found that the new 1-arylpyrazoles of the general formula (I)

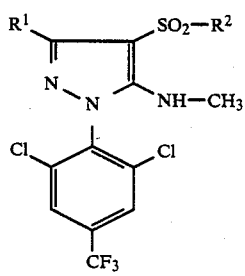

in which
$R^1$ represents alkyl and
$R^2$ represents halogenoalkyl,
are obtained when
(a) 5-amino-1-aryl-pyrazoles of the formula (II)

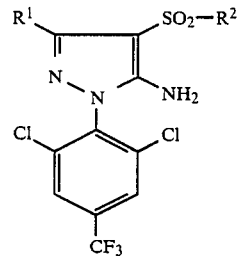

in which
$R^1$ and $R^2$ have the abovementioned meaning, are reacted with methylating agents of the formula (III)

$$CH_3-E \qquad (III)$$

in which
E represents an electron-withdrawing leaving group, if appropriate in the presence of a diluent and if appropriate in the presence of an acid-binding agent and also if appropriate in the presence of a catalyst; or when
(b) 5-(N-acylamino)-1-arylpyrazoles of the formula (IV)

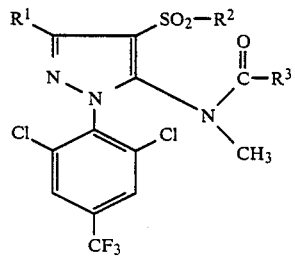

in which
$R^1$ and $R^2$ have the abovementioned meaning and
$R^3$ represents alkyl,
are deacylated using acids as catalysts, if appropriate in the presence of a diluent; or when
(c) 1-arylpyrazoles of the formula (V)

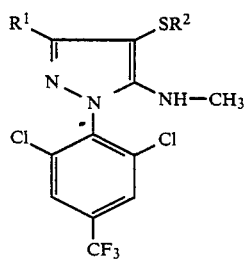

in which
$R^1$ and $R^2$ have the abovementioned meaning, are reacted with an oxidant, if appropriate in the presence of a diluent and if appropriate in the presence of a catalyst and also if appropriate in the presence of an acid-binding agent; or when
(d) 5-halogeno-1-arylpyrazoles of the formula (VI)

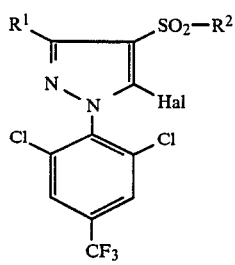

in which
R¹ and R² have the abovementioned meaning and
Hal represents halogen,
are reacted with methylamine of the formula (VII)

 (VII)

if appropriate in the presence of a diluent and if appropriate in the presence of an acid-binding agent.

Finally, it has been found that the new substituted 5-methylamino-1-arylpyrazoles of the formula (I) possess a very good action against animal pests.

Surprisingly, the substituted 5-methylamino-1-arylpyrazoles according to the invention show a considerably better action against animal pests than the 1-arylpyrazoles known from the prior art, such as, for example, 1-(2,6-dichloro-4-trifluoromethylphenyl)-5-methylamino-4-dichlorofluoromethylthio-pyrazole or 1-(2,6-dichlo-4-trifluoromethylphenyl)-5-methylamino-4-trifluoromethylthio-pyrazole, which are related compounds chemically and with respect to their action.

Formula (I) provides a general definition of the substituted 5-methylamino-1-arylpyrazoles according to the invention. Preferred compounds of the formula (I) are those in which $R^1$ represents straight-chain or branched alkyl having 1 to 4 carbon atoms and $R^2$ represents straight-chain or branched halogenoalkyl having 1 to 4 carbon atoms and 1 to 9 identical or different halogen atoms.

Particularly preferred compounds of the formula (I) are those in which $R^1$ represents methyl or ethyl and $R^2$ represents chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl, bromopropyl, dichloromethyl, chlorofluoromethyl, trichloromethyl, trifluoroethyl, trifluorochloroethyl, tetrafluoroethyl, difluorochloroethyl, fluorodibromomethyl, difluorobromomethyl or fluorochlorobromomethyl.

Very particularly preferred compounds of the formula (I) are those in which $R^1$ represents methyl and $R^2$ represents trifluoromethyl, dichlorofluoromethyl or difluorochloromethyl.

If, for example, 5-amino-3-methyl-4-trifluoromethylsulphonyl-1-(2,6-dichloro-4-trifluoromethylphenyl)-pyrazole and methyl iodide are used as starting materials, then the course of the reaction of process (a) according to the invention can be represented by the following equation:

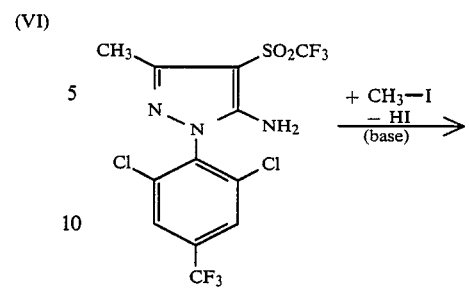

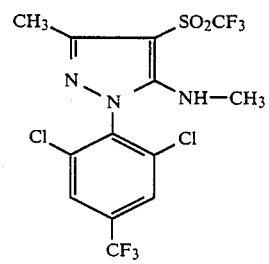

If, for example, 3-methyl-4-trifluoromethylsulphonyl-5-(N-methyl-acetamido)-1-(2,6-dichloro-4-trifluoromethylphenyl)-pyrazole is used as the starting compound, then the course of the (b) according to the invention can be represented by the following equation:

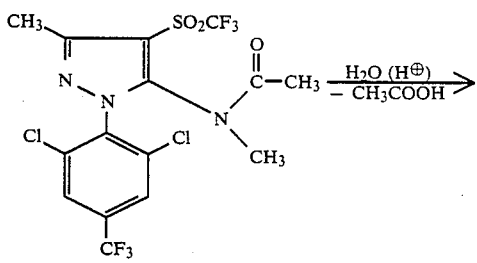

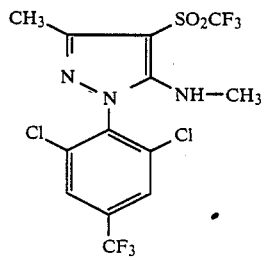

If, for example, 3-methyl-5-methylamino-4-trifluoromethylthio-1-(2,6-dichloro-4-trifluoromethylphenyl)-pyrazole is used as the starting compound and m-chloroperbenzoic acid as the oxidant, then the course of the reaction of process (c) according to the invention can be represented by the following equation:

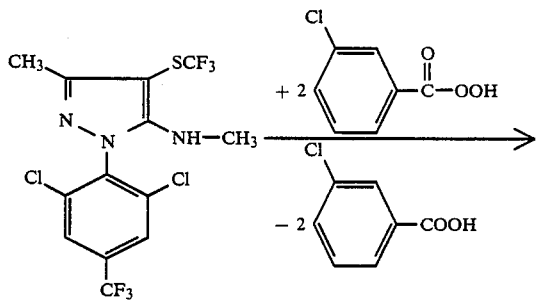

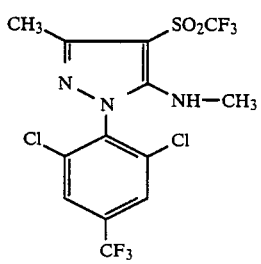

If, for example, 4-dichlorofluoromethylsulphonyl-5-bromo-3-methyl-1-(2,6-dichloro-4-trifluoromethyl-phenyl)pyrazole and methylamine are used as starting materials, then the course of the reaction of process (d) according to the invention can be represented by the following equation:

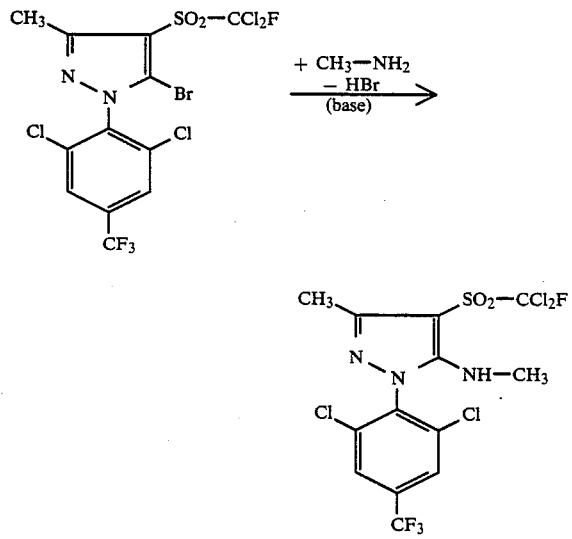

Formula (II) provides a general definition of the 5-amino-1-arylpyrazoles required as starting materials for carrying out process (a) according to the invention. In this formula (II), $R^1$ and $R^2$ preferably represent those radicals which have already been mentioned as preferred for these substituents in connection with the description of the substances of the formula (I) according to the invention.

The 5-amino-1-aryl-pyrazoles of the formula (II) are known (compare EP 201,852).

Formula (III) provides a general definition of the methylating agents furthermore required as starting materials for carrying out process (a) according to the invention. In this formula (III), E preferably represents halogen, in particular chlorine, bromine or iodine, or methoxysulphonyloxy or p-toluenesulphonyloxy.

The methylating agents of the formula (III) are generally known compounds of organic chemistry Formula (IV) provides a general definition of the 5-(N-acylamino)-1-arylpyrazoles required as starting materials for carrying out process (b) according to the invention. In this formula (IV), $R^1$ and $R^2$ preferably represent those radicals which have already been mentioned as preferred for these substituents in connection with the description of the substances of the formula (I) according to the invention $R^3$ preferably represents straight-chain or branched alkyl having 1 to 4 carbon atoms, in particular methyl or ethyl.

The 5-(N-acylamino)-1-arylpyrazoles of the formula (IV) were hitherto unknown. However, they are obtained analogously to known processes (compare, for example, EP 201,852), when 5-(N-acylamino)-pyrazoles of the formula (VIII)

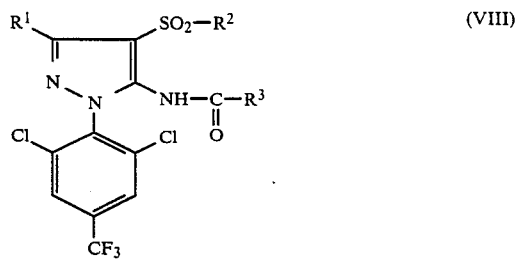

in which $R^1$, $R^2$ and $R^3$ have the abovementioned meaning, are reacted with methylating agents of the formula (III)

$$CH_3\text{—}E \quad \text{(III)}$$

in which

E represents an electron-withdrawing leaving group, such as, for example, halogen, in particular chlorine, bromine or iodine, or methoxysulphonyloxy or p-toluenesulphonyloxy, analogously to carrying out process (a) according to the invention, if appropriate in the presence of a diluent such as, for example, dichloromethane and if appropriate in the presence of a base such as, for example, sodium hydroxide solution and also if appropriate in the presence of a phase-transfer catalyst such as, for example, tributylbenzylammonium chloride at temperatures between 0° C. and 120° C.

The 5-(N-acylamino)-pyrazoles of the formula (VIII) are known (compare EP 201,852).

The formula (V) provides a general definition of the 1-arylpyrazoles required as starting materials for carrying out process (c) according to the invention. In this formula (V), $R^1$ and $R^2$ preferably represent those radicals which have already been mentioned as preferred for these substituents in connection with the description of the substances of the formula (I) according to the invention.

The 1-arylpyrazoles of the formula (V) are known or obtainable analogously to known processes (compare EP 201,852), for example when 5-amino-1-aryl-pyrazoles of the formula (IX)

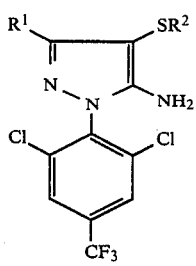

in which

R¹ and R² have the abovementioned meaning, are initially reacted with acylating agents of the formula (X)

(X)

in which

R³ represents alkyl, in particular methyl or ethyl and

X represents an electron-withdrawing leaving group such as halogen or alkylcarbonyloxy, in particular chlorine, acetoxy or propionyloxy, if appropriate in the presence of a diluent such as, for example, dichloromethane and if appropriate in the presence of an acid-binding agent such as, for example, triethylamine at temperatures between −20° C. and +120° C., the 5-(N-acylamino)-1-arylpyrazoles of the formula (XI)

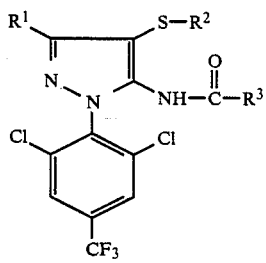

in which

R¹, R² and R³ have the abovementioned meaning, thus obtainable are then methylated using methylating agents of the formula (III)

(III)

in which

E represents an electron-withdrawing leaving group, such as in particular iodine, methoxysulphonyloxy or p-toluenesulphonyloxy, analogously to carrying out process (a) according to the invention, if appropriate in the presence of a diluent such as, for example, acetonitrile and if appropriate in the presence of an acid-binding agent such as, for example, potassium carbonate at temperatures between 0° C. and 180° C., and the 1-aryl-pyrazoles of the formula (XII

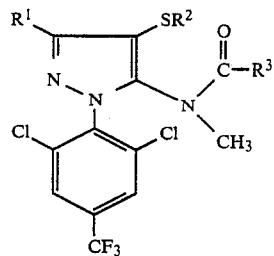

in which

R¹, R² and R³ have the abovementioned meaning, thus obtainable are finally deacylated using acids such as, for example, sulphuric acid analogously to carrying out process (b) according to the invention if appropriate in the presence of a diluent such as, for example, methanol at temperatures between 0° C. and 120° C.

The 5-amino-1-aryl-pyrazoles of the formula (IX) are known, as are the 5-(N-acylamino)-1-arylpyrazoles of the formula (XI) (compare EP 201,852).

The acylating agents of the formula (X) are generally known compounds of organic chemistry.

Formula (VI) provides a general definition of the 5-halogeno-1-arylpyrazoles required as starting materials for carrying out process (d) according to the invention. In this formula (VI), R¹ and R² preferably represent those radicals which have already been mentioned as preferred for these substituents in connection with the description of the substances of the formula (I) according to the invention.

Hal preferably represents chlorine or bromine.

The 5-halogeno-1-aryl-pyrazoles of the formula (VII) are known (compare DE-OS (German Published Specification No.) 3,529,829).

Methylamine of the formula (VII), furthermore required as the starting compound for carrying out process (d) according to the invention, is a generally known compound of organic chemistry.

Suitable diluents for carrying out process (a) according to the invention are inert organic solvents. These include in particular aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or sulphoxides, such as dimethyl sulphoxide.

Process (a) according to the invention can also be carried out if appropriate in a two-phase system, such as, for example, water/toluene or water/dichloromethane, or if appropriate in the presence of a phasetransfer catalyst. Catalysts which may be mentioned as examples are: tetrabutylammonium iodide, tetrabutylammonium bromide, tributyl-methylphosphonium bromide, trimethyl-$C_{13}/C_{15}$-alkylammonium chloride, dibenzyl-dimethyl ammonium methylsulphate, dimethyl-$C_{12}/C_{14}$-alkyl-benzylammonium chloride, tetrabutylammonium hydroxide, 15- crown-5, 18-crown-6, triethylbenzylammonium chloride and trimethylbenzylammonium chloride.

Suitable acid-binding agents for carrying out process (a) according to the invention are all conventionally utilizable inorganic and organic bases. Hydrides, hydroxides, amides, alcoholates, carbonates or hydrogen carbonates of alkali metals, such as, for example, sodium hydride, sodium amide, sodium methylate, sodium hydroxide, sodium carbonate or sodium hydrogen carbonate and also tertiary amines, such as, for example, triethylamine, N,N-dimethylaniline, pyridine, 4-(N,N-dimethylamino)pyridine, diazabicyclooctane (DABCO), diazabicyclononene (DBN) or diazabicycloundecene (DBU) are preferably used.

The reaction temperatures can be varied within a relatively wide range when carrying out process (a) according to the invention. In general the reaction is carried out between $-20°$ C. and $+150°$ C., preferably between $0°$ C. and $+100°$ C.

When carrying out process (a) according to the invention, 1.0 to 20.0 mols, preferably 1.0 to 15.0 mols, of methylating agent of the formula (III) and if appropriate 1.0 to 3.0 mols, preferably 1.0 to 2.0 mols of acid-binding agent and also 0.01 to 1.0 mol of phase-transfer catalyst are generally employed per mol of 5-amino-1-arylpyrazole of the formula (II). The reaction is carried out and the reaction products of the formula (I) are worked up and isolated in a conventional manner.

Suitable diluents for carrying out the process (b) according to the invention are inorganic or organic polar solvents. Alcohols, such as, for example, methanol, ethanol or propanol, or their mixtures with water, or pure water are preferably used as the diluent.

Suitable catalysts for carrying out process (b) according to the invention are preferably inorganic mineral acids, in particular hydrochloric acid or sulphuric acid.

The reaction temperatures can be varied within a relatively wide range when carrying out process (b) according to the invention. In general, the reaction is carried out between $+20°$ C. and $+150°$ C., preferably between $+50°$ C. and $+120°$ C.

When carrying out process (b) according to the invention, 1.0 to 20.0 mols, preferably 1.0 to 10.0 mols, of acid catalyst are generally employed per mol of 5-(N-acylamino)-1-aryl-pyrazole of the formula (IV), and the mixture is warmed for several hours at the necessary reaction temperature. The reaction products of the formula (I) are worked up, isolated and purified by customary methods.

The oxidants used for carrying out process (c) according to the invention are all inorganic or organic oxidants which are customarily suitable for sulphur oxidations. Organic peracids, such as, for example, peracetic acid, 4-nitroperbenzoic acid or 3-chloroperbenzoic acid, inorganic peracids, such as, for example, periodic acid or hydrogen peroxide, potassium permanganate or chromic acid are preferably used.

Suitable diluents for carrying out process (c) according to the invention are likewise inert organic solvents. Hydrocarbons, such as benzine, benzene, toluene, hexane or petroleum ether; chlorinated hydrocarbons, such as dichloromethane, 1,2-dichloroethane, chloroform, carbon tetrachloride or chlorobenzene; ethers, such as diethyl ether, dioxane or tetrahydrofuran; carboxylic acids, such as acetic acid or propionic acid, or dipolar aprotic solvents, such as acetonitrile, acetone, ethyl acetate or dimethylformamide are preferably used.

If desired, process (c) according to the invention can be carried out in the presence of an acid-binding agent. Those suitable are all customarily utilizable organic and inorganic acid-binding agents. Hydroxides, acetates or carbonates of alkaline earth metals or alkali metals, such as, for example, calcium hydroxide, sodium hydroxide, sodium acetate or sodium carbonate are preferably used.

If desired, process (c) according to the invention can be carried out in the presence of a suitable catalyst. Those suitable are all catalysts conventionally suitable for sulphur oxidations of this type. Heavy-metal catalysts such as ammonium molybdate may be mentioned by way of example in this connection.

The reaction temperatures can be varied within a relatively wide range when carrying out process (c) according to the invention. In general, the reaction is carried out at temperatures between $-20°$ C. and $+70°$ C., preferably at temperatures between $0°$ C. and $+50°$ C.

When carrying out process (c) according to the invention, 1.8 to 5.0 mols, preferably twice the molar amount, of oxidants are generally employed per mol of 1-arylpyrazole of the formula (V). The reaction is carried out, and the final products of the formula (I) are worked up and isolated by customary processes.

Suitable diluents for carrying out process (d) according to the invention are inert organic solvents. These include in particular aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate or sulphoxides such as dimethyl sulphoxide.

If desired, process (d) according to the invention can be carried out in the presence of a suitable acidbinding agent. Those suitable are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethyl-amine, N,N-dimethylaniline, pyridine, N,N-dimethylaminopyridine, diazabicyclooctane (DABCO), diazabicyclononene (DBN) or diazabicycloundecene (DBU). However, it is also possible simultaneously to use a suitable excess of methylamine of the formula (VII) employed as the reaction partner as the acidbinding agent.

The reaction temperatures can be varied within a relatively wide range when carrying out process (d) according to the invention. In general, the reaction is carried out at temperatures between $-20°$ C. and $+200°$ C., preferably at temperatures between $0°$ C. and $+150°$ C.

When carrying out process (d) according to the invention, 1.0 to 10.0 mols, preferably 1.0 to 5.0 mols of methylamine of the formula (VII) are generally employed per mol of 5-halogeno-1-aryl-pyrazole of the formula (VI). The reaction is carried out, and the reaction products of the formula (I) are worked up and isolated by usual processes.

The active compounds according to the invention are suitable for combating animal pests, in particular insects and nematodes, encountered in agriculture, in forestry, in the protection of stored products and of materials, and in the hygiene field, and have good plant tolerance and favourable toxicity to warm-blooded animals. They are active against normally sensitive and resistant species and against all or some stages of development. The abovementioned pests include:

From the above order of the Isopoda, for example, *Oniscus asellus, Armadillidium vulgare* and *Porcellio scaber*. From the order of the Diploda, for example, *Blaniulus guttulatus*. From the order of the Chilopoda, for example, *Geophilus carpophagus* and *Scutigera spec.* From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella gernanica, Acheta domesticus, Gryllotalpa spp., Locusta migratoria migratorioides, Melanoplus differentialis* and *Schistocerca gregaria*. From the order of the Dermaptera, for example, *Forficula auricularia*. From the order of the Isoptera, for example, *Reticulitermes spp.*. From the order of the Anoplura, for example, *Phylloxera vastatrix, Pemphigus spp., Pediculus humanus corporis, Haematopinus spp.* and *Linognathus spp*. From the order of the Mallophaga, for example, *Trichodectes spp.* and *Damalinea spp*. From the order of the Thysanoptera, for example, *Hercinothrips femoralis* and *Thrips tabaci*. From the order of the Heteroptera, for example, *Eurygaster spp., Dysdercus intermedius, Piesma quadrata, Cimex lectularius, Rhodnius prolixus* and *Triatoma spp*. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp*. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Laphygma-exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Bruchidius obtectus, Acanthoscelides obtectus Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethec aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica*. From the order of the Hymenoptera, for example, *Diprion spp., Hoplocampa spp., Lasius spp., Monomorium pharaonis* and *Vespa spp*. From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus. Oscinella frit, Phorbia spp., Pegomyia hyoscyami, Ceratitis capitata, Dacus oleae* and *Tipula paludosa*. From the order of the Siphonaptera, for example, *Xenopsylla cheopis* and *Ceratophyllus spp*.

Plant-parasitic nematodes include *Pratylenchus spp., Radopholus similis, Ditylenchus dipsaci, Tylenchulus semipenetrans, Heterodera spp., Meloidogyne spp., Aphelenchoides spp., Longidorus spp., Xiphinema spp.* and *Trichodorus spp*.

The active compounds according to the invention are not only active against plant, hygiene and stored product pests, but also, in the veterinary medicine sector, against animal parasites (ectoparasites and endoparasites), such as scaly ticks, argasidae, scab mites, trombidae, flies (stinging and sucking), parasitic fly larvae, lice, hair lice, bird lice and fleas.

They are active against normally sensitive and resistant species and strains, as well as against all parasitic and non-parasitic stages of development of the ectoparasites and endoparasites.

The active compounds of the formula (I) utilizable according to the invention are distinguished by a strong insecticidal action. They can be employed in particular against insects which are harmful to plants, such as, for example, against the larvae of the mustard beetle (*Phaedon cochleariae*). In addition, they are also extremely suitable for combating soil insects.

In addition, the active compounds of the formula (I) utilizable according to the invention have a high activity against hygiene pests and stored product pests and can be employed, for example, for combating mosquito larvae (*Aedes aegypti*).

Moreover, the active compounds according to the invention can be particularly successfully used for combating pests which live parasitically on warm-blooded animals, such as, for example, against the larvae of the sheep maggot fly (*Lucilia cuprina*), against stable flies (*Stomoxys calcitrans*), against the facefly (*Musca autumnalis*) or against cattle ticks (*Boophilus microplus*) and also against nematodes which live endoparasitically.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight. The compounds are employed in a customary manner appropriate for the use forms.

When used against hygiene pests and pests of stored products, the active compounds are distinguished by an excellent residual action on wood and clay as well as a good stability to alkali on limed substrates.

The active compounds which can be used according to the invention are also suitable for combating insects, midges, ticks etc. in the sectors of animal keeping and cattle breeding; better results, for example higher milk production, greater weight, more attractive animal pelt, longer life etc., can be achieved by combating the pests.

The administration of the active compounds according to the invention occurs in this sector in a known fashion, such as by oral administration in the form of, for example, tablets, capsules, potions, granules, by means of dermal or external application in the form of, for example, dipping, spraying, pouring-on, spotting-on and dusting, as well as by means of parenteral administration in the form, for example, of injection, and, furthermore, by means of the feed-through process. In addition, application as molded articles (collar, ear tag) is also possible.

The biological effectiveness of the compounds according to the invention will be explained with reference to the examples below.

PREPARATION EXAMPLES

Example 1

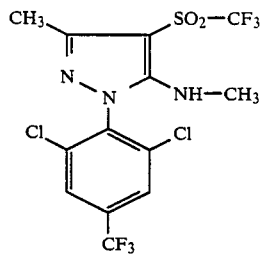

(Process b)

5.1 g(0.01 mol) of 5-(N-propionyl-N-methylamino)-3-methyl-4-trifluoromethylsulphonyl-1-(2,6-dichloro-4-trifluoromethylphenyl)-pyrazole are stirred for 20 hours at room temperature in 30 ml of 80 per cent strength aqueous sulphuric acid. For working up, the reaction mixture is poured into ice-water and repeatedly extracted with dichloromethane, the combined organic phases are washed with saturated aqueous sodium hydrogen carbonate solution and dried over magnesium sulphate, and the solvent is removed in vacuo.

4 g (88% of theory) of 5-methylamino-3-methyl-4-trifluoromethylsulphonyl-1-(2,6-dichloro-4-trifluoromethylphenyl-pyrazole of melting point 139° C.–140° C. are obtained.

Alternative preparation:
(Process c)

20.6 ml (0.18 mol) of 30 per cent strength aqueous hydrogen peroxide solution are added at room temperature to 25 g (0.059 mol) of 5-methylamino-3-methyl-4-trifluoromethylthio-1-(2,6-dichloro-4-trifluoromethylphenyl)-pyrazole (compare EP 201,852, in 80 ml of 80 per cent strength sulphuric acid, and the reaction mixture is stirred for 12 hours at 60° C. and poured into ice-water; the mixture is extracted using dichloromethane, washed with aqueous sodium hydrogen carbonate solution and dried over magnesium sulphate, and the solvent is removed in vacuo.

20 g (74% of theory) of 5-methylamino-3-methyl4-trifluoromethylsulphonyl-1-(2,6-dichloro-4-trifluoromethylphenyl)-pyrazole of melting point 139° C.–140° C. are obtained.

Preparation of the starting compound

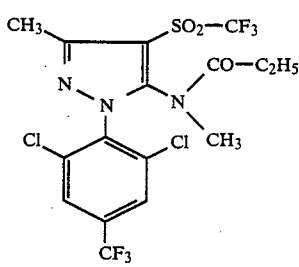

237 ml of 45 per cent strength aqueous sodium hydroxide solution, 0.5 g of tributylbenzylammonium chloride and 30 ml (0.315 mol) of dimethyl sulphate are added at room temperature with stirring to 149.4 g (0.3 mol) of 3-methyl-5-propionamido-1-(2,6-dichloro-4-trifluoromethylphenyl)-4-trifluoromethylsulphonyl-pyrazole (compare EP 201,852) in 950 ml of dichloromethane, the reaction mixture is stirred for 2 hours at room temperature, 500 ml of dichloromethane and 300 ml of water are added, and the mixture is stirred for a further 30 minutes For working up, the organic phase is separated off, washed using 500 ml of 2 per cent strength hydrochloric acid and 500 ml of saturated aqueous sodium chloride solution, dried over magnesium sulphate and freed from solvent in vacuo.

142.8 g (93% of theory) of 5-(N-propionyl-N-methylamino)-3-methyl-4-trifluoromethylsulphonyl-1-(2 6-dichloro-4-trifluoromethylphenyl)-pyrazole are obtained as oil, which is reacted further without additional purification.

Example 2

The compound 5-methylamino-3-methyl-4-dichlorofluoromethylsulphonyl-1-(2,6-dichloro-4-trifluoromethylphenyl)-pyrazole of the formula

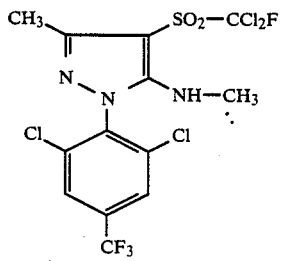

can be obtained similarly.

Use Examples

The compounds shown below were employed as comparison substances in the following use examples:

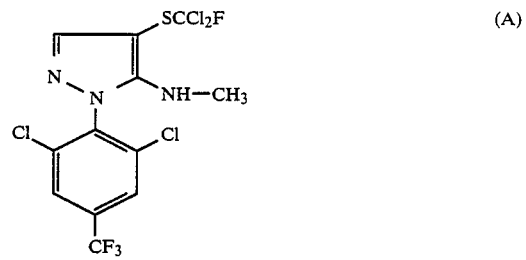

1-(2,6-Dichloro-4-trifluoromethylphenyl)-5-methylamino-4dichlorofluoromethylthio-pyrazole

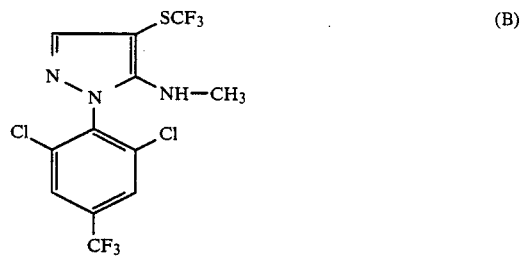

1-(2,6-Dichloro-4-trifluoromethylphenyl)-5-methylamino-4-trifluoromethylthio-pyrazole (both known from EP 201,852)

Example A

Mosquito larvae test

Test insects: 4th Larval stage of *Aedes aegypti*

Solvent: 99 parts by weight of acetone

Emulsifier: 1 part by weight of benzylhydroxydiphenyl polyglycol ether

To produce a suitable preparation of active compound, 2 parts by weight of active compound are dissolved in 1,000 parts by volume of the solvent, containing the amount of emulsifier stated above. The solution thus obtained is diluted with water to the desired lower concentrations.

The aqueous preparations of active compound of the desired concentration are filled into plastic beakers and about 25 mosquito larvae are then placed in each beaker. The larvae are fed daily with fish food (Tetramin ®).

After 24 hours, the destruction in % is determined. 100% means that all larvae have been killed. 0% means that no larvae at all have been killed.

In this test, for example, the following compound from the preparation examples shows a superior action compared to the prior art: 1.

Example B

Phaedon larvae test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the specified periods of time, the destruction in % is determined. 100% means that all the beetle larvae have been killed; 0% means that none of the beetle larvae have been killed.

In this test, for example, the following compound from the preparation examples shows superior activity compared to the prior art: 1.

Example C

Test with *Lucilia cuprina* res. larvae
Emulsifier:
35 parts by weight of ethylene glycol monomethyl ether
35 parts by weight of nonylphenol polyglycol ether To produce a suitable preparation of active compound, three parts by weight of active compound are mixed with seven parts by weight of the abovementioned solvent mixture and the concentrate thus obtained is diluted with water to the particular desired concentration.

About 20 *Lucilia cuprina* res. larvae are introduced into a test tube which contains approx. 1 cm$^3$ of horse muscle and 0.5 ml of the preparation of active compound. After 24 hours, the degree of destruction is determined.

In this test, for example, the following compound from the preparation examples shows superior action compared to the prior art: 1.

Example D

Test with *Boophilus microplus* resistant. (OP-resistant Biarra Strain)
Solvent:
35 parts by weight of ethylene glycolmonomethyl ether
35 parts by weight of nonylphenol polyglycol ether To produce a suitable preparation of active compound, three parts by weight of active compound are mixed with seven parts by weight of the solvent mixture indicated above, and the concentrate thus obtained is diluted with water to the desired concentration.

10 adult *Boophilus microplus* res. are immersed for 1 minute in the active compound preparation to be tested. After transfer to plastic beakers and storage in a climatically controlled chamber, the degree of destruction is determined.

In this test, for example, the following compound from the preparation examples shows a superior activity compared to the prior art: 1.

Example E

Test with parasitic, adult stable flies (*Stomoxys calcitrans*)
Solvent: Cremophor To produce a suitable preparation of active compound, the active substance concerned is mixed with the abovementioned solvent in the ratio 1:2 and the concentrate thus obtained is diluted with water to the particular desired concentration.

10 adult stable flies *Stomoxys calcitrans* are placed in Petri dishes containing sandwiches of appropriate size which have been saturated one day before the start of the experiment with 1 ml of the active compound preparation to be tested. After 3 hours, the degree of destruction is determined, 100% denoting that all the flies have been killed and 0% denoting that none have been killed.

In this test, the following compound of the preparation examples, for example, displays superior action compared to the prior art: 2.

Example F

Facefly test (*Musca autumnalis*)
Solvent:
35 parts by weight of ethylene glycol monomethyl ether
35 parts by weight of nonylphenol polyglycol ether To produce a suitable formulation, three parts by weight of active compound are diluted with seven parts of the abovementioned solvent/emulsifier mixture and the emulsion concentrate thus obtained is diluted with water to the particular desired concentration.

10 adult faceflies (*Musca autumnalis*) are introduced into Petri dishes containing filter paper discs of appropriate size which have been impregnated one day before the start of the test with 1 ml of the active compound preparation to be tested. After 3 hours, the degree of destruction is determined in per cent, 100% meaning that all of the flies have been destroyed and 0% meaning that no flies have been destroyed.

In this test, for example, the following compound from the preparation examples shows a superior action compared to the prior art: 1.

Example G

In vitro nematode test
*Caenorhabditis elegans*

$10^{-4}$ g of active compound are dissolved in 1 ml of water or 0.1 ml of dimethyl sulphoxide (DMSO). This solution is poured onto a replica plate. 2 ml of E. coli suspension to which 10–20 female animals or larvae of *Caenorhabditis elegans* in 0.5 ml of sterile M9 buffer solution have been added are introduced onto the plate. The E. coli suspension is prepared by adding 1.8 l of sterile M9 buffer solution to 300 ml of an overnight culture of a uracil-dependent E. coli strain.

The test batch is incubated for 7 days at 22° C. and then evaluated. The extent to which the active compound impairs reproduction is evaluated, and the concentration at which reproduction is inhibited is given.

In this test, for example, the following compound from the preparation examples shows at least 95% inhibition of reproduction of the nematode C. elegans - at a concentration of $\leq 10 \mu g/ml$: 1.

It is understood that the specification and examples are illustrative but not limitative of the present invention and that other embodiments within the spirit and scope of the invention will suggest themselves to those skilled in the art.

We claim:

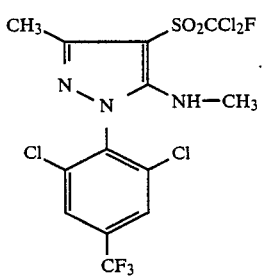

1. The compound 5-methylamino-3-methyl-4-dichlorofluoromethylsulphonyl-1-(2,6-dichloro-4-trifluoromethylphenyl)-pyrazole of the formula 2. A pesticidal composition comprising a pesticidally effective amount of a compound according to claim 1 and a diluent.

3. A method of combating pests which comprises applying to such pests or to a pest habitat a pesticidally effective amount of a compound according to claim 1.

* * * * *